United States Patent [19]

Visscher

[11] 4,209,530

[45] Jun. 24, 1980

[54] INSECT CONTROL COMPOSITIONS EMPLOYING ABSCISIC ACID

[75] Inventor: Saralee N. Visscher, Bozeman, Mont.

[73] Assignee: Endowment and Research Foundation at Montana State University, Bozeman, Mont.

[21] Appl. No.: 929,116

[22] Filed: Jul. 28, 1978

[51] Int. Cl.$^2$ ............................................... A01N 9/24
[52] U.S. Cl. ............................ 424/317; 424/DIG. 12
[58] Field of Search ......................... 424/317, DIG. 12

[56] References Cited

U.S. PATENT DOCUMENTS 3,958,025  5/1976  Livingston ............................ 424/317

OTHER PUBLICATIONS

Eidt et al., "J. Econ. Ent.," vol. 63, No. 6 (1970), pp. 1966–1968.
Eidt et al., "The Canadian Entomologist," vol. 100, pp. 1278–1279 (1968).

*Primary Examiner*—V. D. Turner
*Attorney, Agent, or Firm*—Lowe, King, Price & Becker

[57] ABSTRACT

There are disclosed insect control compositions comprising abscisic acid and its analogs, and a method of controlling insects by inhibiting the reproduction thereof which comprises applying abscisic acid or an analog to plants on which the insects will feed.

6 Claims, No Drawings

INSECT CONTROL COMPOSITIONS EMPLOYING ABSCISIC ACID

FIELD OF THE INVENTION

This invention relates to a novel insect control composition and to a novel method for the control of insects. More particularly, the invention relates to a composition containing abscisic acid and/or its analogs and to a method of inhibiting the reproduction of insects or to cause their deaths to achieve insect control.

BACKGROUND ART

Abscisic acid is a naturally occurring plant hormone which has been found to be useful in the treatment of a vitamin deficiency in man, animal and the avian species. See U.S. Pat. No. 3,958,025 to Livingston. This hormone has been used to delay budbreak of certain plants and thereby to exert an insect control effect. This approach is based upon reducing the food supply available to phytophagous insects. See D.C. Eidt and C.H.A. Little, *The Canadian Entomologist*, 100, 1278-1279 (1968). This hormone has also been tested for its effect, when ingested, on spruce budworm. See D.C. Eidt and C.H.A. Little, *Journal of Economic Entomology*, 63, 1966-1968 (1970). Eidt and Little conclude that the development of the budworm is not affected and state that their data is inconclusive as to affects on pupal size, development time, fecundity, and egg viability since the number of budworms tested was too small. S. Scheurer, in *The Host-Plant in Relation to Insect Behavior and Reproduction*, T. Jeremy, Ed., Plenum Press, New York, pp. 255-259 (1976), reports that when plants of Vicia sp. are treated with abscisic acid and fed to aphids, there is observed an increased size of the $V_1$ offspring, a decrease in maturation time, and an increase in reproduction of the $V_1$ offspring. The chemistry and physiology of abscisic acid and its analogs are described by Milborrow, *Ann. Rev. Plant Physiol.*, 1974, 25. 259-307.

In addition to the above art, I am aware of approaches to insect control which require chemical substances such as the chlorinated hydrocarbons. These approaches, however, have the disadvantage of employing substances which are not limited in toxicity to insects.

DISCLOSURE OF INVENTION

It is accordingly one object of the present invention to provide a composition for insect control which is toxic to insects based on the amounts applied.

A further object of the present invention is to provide a composition for insect control which is not limited only to its effect on those insects directly affected. Such a composition will result in decreased insect population by death when ingested at high doses by the insect, or when ingested in smaller doses, will result in sterility.

A still further object of the present invention is to provide a method for insect control which has both limited and complete toxicity to insects.

Other objects and advantages of the present invention will become apparent as the description thereof proceeds.

In satisfaction of the foregoing objects and advantages, there is provided by this invention compositions for controlling insects comprising a reproduction inhibiting and nonlethal amount of abscisic acid or its analogs, or a toxic effect at high dosage amounts. There is further provided a method for controlling insects by affecting the reproduction thereof, said method comprising the application to plants of a reproduction inhibiting amount of abscisic acid. Also provided is a method of controlling insects by application of plants of a lethal amount of abscisic acid.

DETAILED DESCRIPTION OF THE INVENTION

As indicated above, the present invention is concerned with a novel insect control composition and with a novel method for controlling insects by inhibiting the reproduction thereof. The present invention is based upon the surprising discovery that abscisic acid and/or its analogs, when ingested, inhibits the reproduction of insects in low dosage amounts, and is lethal in high dosage amounts. According to the present invention, there is provided an insect control composition containing abscisic acid, its analogs, and/or derivatives, and there are provided insect control methods comprising applying abscisic acid to plants.

Abscisic acid is a naturally occurring plant hormone which is found in certain parts of many varieties of plants. Abscisin II and dormin are names previously used for this plant hormone. The structural formula of the hormone is set forth below.

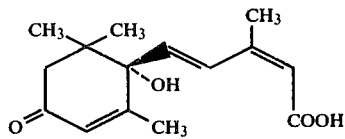

Abscisic Acid

Abscisic acid is known to cause leaf abscission. It is also known to produce a state of dormancy in roots and leaves and to cause ripening of fruits. The action of abscisic acid in producing dormancy opposes the growth promoting action of gibberellic acid, another naturally occurring plant hormone. The hormone has been isolated from those plants in which it naturally occurs and has also been synthesized. For use in the present invention, either the naturally occurring or synthetic forms or analogs which have the same biological activity as a result of their similar molecular structure, such as phaseic acid, dihydrophaseic acid, abscisic alcohol, or aldehyde or xanthoxin compounds, are suitable. All of these materials have the basic nucleus of abscisic acid. Mixtures may also be used. Stereoisomers and mixtures thereof are included within the term abscisic acid.

In the present invention, the abscisic acid can be used either by itself or with suitable carriers and/or additives. Suitable carriers and additives may be solid or liquid, and correspond to the substances common in formulation practice, such as solvents, dispersing agents, wetting agents, adhesives, thickeners and binders. Other additives may be employed to reduce spray drift and aerosol formation and regulate viscosity, according to known practices.

Formulations which can be prepared include solid preparations such as dusts, scattering agents and granulates of several types. Liquid preparations can also be formulated. Examples of liquid preparations are solutions and water dispersible concentrates such as wettable powders, pastes and emulsions. These formulations are made in a manner commonly known in practice and in this regard the disclosures of U.S. Pat. Nos. 3,973,028 and 3,975,522 are hereby incorporated by reference. Generally, these formulations are produced in a manner known per se by the intimate mixing and/or grinding of the hormone with a suitable carrier, optionally with the addition of dispersing agents or solvents which are inert to the hormone.

Conveniently, the abscisic acid-containing composition is stored and shipped in the form of water-dispersible solutions or wettable powders and is diluted with water just prior to spraying. In order to obtain a uniform application of the hormone, it is best to apply it to plants using a carrier or diluent. Water is a very suitable carrier or diluent, but the addition of compounds to render the abscisic acid impermeable to the plant may be necessary in some instances to avoid altering plant growth.

A suitable means of applying the composition of the present invention to a host plant is by spraying. One type of spraying system which is well known in the art is foliar spraying, as illustrated by U.S. Pat. No. 3,973,028. However, there may be used any other means of application by which the composition is made available for ingestion by the insect.

The amount of abscisic acid required in the insect control composition is an amount which inhibits the reproduction of the insect being treated and which is nonlethal to the insect or lethal when ingested in large amounts. From the illustrative embodiment set forth below, a standard is provided by which a worker skilled in the art can select the concentration which will meet his needs.

From these statements, it will be understood that the abscisic acid material can be applied to plants which are fed on by insects in inhibiting reproduction of the insect. In this aspect, the abscisic acid material is applied in sufficient amounts so as to obtain a concentration of from about 6 mg per liter to 60 mg per liter. Concentrations greater than these values, for example, 60 mg to 600 mg per liter, and higher, are effective in being lethal to the insects.

An exemplary insect control composition of the present invention is made by dissolving the selected amount of abscisic acid or equivalent in a small amount of 95% ethanol and then diluting the resulting solution in a large amount of water as the carrier.

It is contemplated that the abscisic acid-containing composition of the present invention is useful for the control of all plant-eating insects and is particularly effective for controlling the grasshopper families of insects, i.e., the Tettigoniidae and Locustidae. Insects included within these general classes are: grasshoppers, katydids, locusts and Mormon crickets. As will be understood, insect control, according to the present invention, is by application of abscisic acid or an analog to a plant on which the insect will feed.

In the following illustrative embodiment of the present invention, the insect control effect of abscisic acid is demonstrated using a grasshopper and its natural host plant, western wheatgrass. It will be appreciated by one skilled in the art that this embodiment is merely illustrative and that there are numerous modifications including those disclosed above which are within the scope of the present invention.

EXAMPLE

The grasshopper, *Aulocara elliotti* (Thomas), was collected as nymphs and as young adults at a wild population site near Simms, Montana, transported to Bozeman, Montana, and divided into groups with three pairs of nymphs maintained per cage until they became adults. The adults are separated one pair to a cage and are maintained under hot temperatures which fluctuate diurnally from 24°–29.5° C.

The growing host plant, western wheatgrass, was transplanted from a field site at the Agricultural Experiment Station Farm near Red Bluff, Montana, onto tables in a greenhouse where it was maintained under hot temperatures which alternate diurnally from approximately 24°–29.5° C.

Twice each week, on Tuesdays and Fridays, grasshopper pairs were fed the greenhouse grass which was freshly cut on the morning of the feeding day and then treated with an abscisic acid-containing composition prepared according to the present invention. The feedings were continued until all grasshoppers were dead. The number of eggs laid and the number of viable eggs were recorded throughout the lifetime of each female grasshopper.

The abscisic acid-containing composition was prepared by dissolving synthetic crystalline abscisic acid (mixed isomers, No. A-7383, Sigma Chemical Company) in 20 ml of 95% ethanol and then diluting the resulting solution to a volume of one liter with distilled water.

The freshly cut greenhouse grass was treated with the composition containing abscisic acid by applying the composition thereto. This was achieved by dipping the grass leaves in the solution and then letting the cut ends stand in the same solution for about 4 hours. Individual feeding vials were assembled by wrapping cut grass with a urethane foam strip about one inch in diameter and then by fitting the bundle of cut grass into a plastic pill vial. The cut grass was then watered with the solution and as this solution evaporated or was taken up by the grass, the vial was rewatered with distilled water.

In this illustrative embodiment, two insect control compositions were formulated which contain 6 mg and 60 mg of abscisic acid per liter. The result of using these compositions is set forth in the following Table. In addition to using compositions containing these two concentrations of abscisic acid, a composition was prepared containing 600 mg of abscisic acid per liter. This higher concentration composition was determined to be lethal to the insect.

The insect control effect of the abscisic acid-containing composition of the present invention was demonstrated by comparison of the above results with a Control, wherein all particulars of the above illustrative embodiment were followed except that the greenhouse grass was not treated with an abscisic acid-containing composition. The result of this Control is set forth in the Table.

By the data set forth in the Table for the abscisic acid-containing compositions and for the Control, the reproduction inhibiting action of abscisic acid is demonstrated. Accordingly, use of an insect control composition containing abscisic acid ranging in concentration from at least about 6 mg per liter to about 60 mg per liter is very suitable in the practice of the present invention, with concentrations in the lower part of the range being preferred to achieve control by inhibiting the reproduction capabilities of the insects. At concentrations above 60 mg per liter, for example, in the range of 600 mg per liter, the abscisic acid composition was lethal to the insect.

The invention has been described herein with reference to certain preferred embodiments. However, as obvious variations will become apparent to those skilled in the art, the invention is not to be considered as limited thereto.

TABLE

| Food Plant and Treatment | Insect Rearing Environment | No. of Adult Pairs | No. of Fertile Pairs | Total Eggs Laid | Mean No. Eggs/Per Female | Total Viable Eggs Laid | Mean No. Viable Eggs/Per Female | Mean Longevity of Fertile Females (Days) | Eggs Laid/ Female Fecund Day | Viable Eggs/ Female Fecund Day |
|---|---|---|---|---|---|---|---|---|---|---|
| Greenhouse grass + Abscisic Acid (ABA) - 6 mg/l | 24°-29.5° C. ("Hot") | 30 | 13 | 138 | 10.6 | 19 | 1.5 | 41.7 | .254 | .035 |
| Green-House grass + ABA - 60 mg/l | "Hot" | 30 | 17 | 247 | 14.5 | 114 | 6.7 | 33.4 | .436 | .201 |
| Green-House grass (No Treatment) | "Hot" | 29 | 21 | 518 | 24.7 | 301 | 14.3 | 36.6 | .674 | .392 |

Having thus set forth and disclosed the nature of this invention, what is claimed is:

1. A method of controlling phytophagous insects selected from the group consisting of the Tettigoniidae and the Locustidae, which comprises applying abscisic acid contained in a carrier to plants wherein the concentration of said abscisic acid in said carrier ranges from about 6 mg per liter to about 60 mg per liter; and permitting said insects to feed on said plants, thereby reducing the ability of the said insects to reproduce and thus control the proliferation of the insects.

2. The method of claim 1 wherein the plant is grass or other vegetation.

3. The method of claim 1 wherein application of the abscisic acid is by spraying.

4. The method of claim 1 wherein the concentration of abscisic acid is about 6 mg per liter.

5. The method of claim 1 wherein the concentration of abscisic acid is about 60 mg per liter.

6. The method of claim 1 wherein the insect is *Aulocara elliotti.*

* * * * *